United States Patent
Ischinger

(10) Patent No.: US 6,176,852 B1
(45) Date of Patent: Jan. 23, 2001

(54) DEVICE FOR IMPROVING HANDLING OF GUIDING WIRES

(76) Inventor: Thomas Ischinger, Oberonstrasse 3, D-81927 Munchen (DE)

( * ) Notice: Under 35 U.S.C. 154(b), the term of this patent shall be extended for 0 days.

(21) Appl. No.: 08/945,658
(22) PCT Filed: Apr. 26, 1996
(86) PCT No.: PCT/EP96/01748
§ 371 Date: Jan. 13, 1998
§ 102(e) Date: Jan. 13, 1998
(87) PCT Pub. No.: WO96/33765
PCT Pub. Date: Oct. 31, 1996

(30) Foreign Application Priority Data

Apr. 28, 1995 (DE) .............................................. 195 15 761

(51) Int. Cl.$^7$ ................................................ A61M 25/00
(52) U.S. Cl. .......................................... 604/523; 600/585
(58) Field of Search .................................. 604/280, 282, 604/192, 162, 164, 165, 171, 93, 158, 159, 523, 524, 525, 528; 606/108; 600/585; 138/120; 343/901; 92/51

(56) References Cited

U.S. PATENT DOCUMENTS

| | | |
|---|---|---|
| 2,179,415 * | 11/1939 | Mace . |
| 4,449,532 * | 5/1984 | Storz . |
| 4,616,652 | 10/1986 | Simpson .............................. 128/344 |
| 4,799,496 * | 1/1989 | Hargreaves et al. ................... 604/95 |
| 5,300,045 * | 4/1994 | Plassche, Jr. ......................... 604/162 |
| 5,358,493 * | 10/1994 | Schweich, Jr. et al. ............. 604/264 |
| 5,382,238 * | 1/1995 | Abrahamson et al. .............. 604/170 |
| 5,725,504 * | 3/1998 | Collins ................................. 604/165 |

FOREIGN PATENT DOCUMENTS 0 416 734 A1 3/1991 (EP) .
WO 95/21566 8/1995 (WO) .

\* cited by examiner

*Primary Examiner*—Sharon Kennedy
(74) *Attorney, Agent, or Firm*—Crompton, Seager & Tufte, LLC

(57) ABSTRACT

A device (1) is disclosed to improve handling of a catheter guiding wire (6) at its proximal end. The device has a base body (9, 11) with a longitudinal lumen (10) for receiving the guiding wire (6), frictional clamping means for clamping the guiding wire in the longitudinal lumen (10), and an extension (11) shaped as a hollow needle that extends in the direction of the longitudinal lumen (10) and that protrudes at the distal and/or proximal end of the base body and is movable in the longitudinal direction in relation thereto. The hollow needle-shaped extension is preferably telescopically collapsible and the clamping means are arranged at the proximal end of the base body (9) in the longitudinal direction.

3 Claims, 1 Drawing Sheet

DEVICE FOR IMPROVING HANDLING OF GUIDING WIRES

BACKGROUND OF THE INVENTION

In ballooning or catheter examinations inside the heart, for example, the balloon catheter or any other catheter is advanced or retracted by means of a so-called guide wire inside a guiding catheter previously introduced in the patient. In the monorail type of balloon catheters, the guide wire exits from the wire-receiving lumen of the balloon catheter about 10 to 30 cm proximally of the baloon (FIG. 1) and then extends outside, but in parallel with, the balloon catheter shank, within the guide catheter up to the proximal end thereof outside the patient so that the surgeon can hold the shank of the balloon catheter and the guide wire side by side (or one behind the other in non-monorail systems) for manipulation by his/her hands at the proximal end of the guide catheter.

As the ballooning or other catheter treatment proceeds, the catheter may have to be withdrawn completely from the guide catheter for replacement, for example. When this is done, it is important for the guide wire to be held—despite the withdrawal of the balloon catheter—in the position it has attained in order to keep the attained location within reach. Withdrawing the (balloon) catheter is unproblematic, initially, and is accomplished by simply holding the guide wire by one hand and withdrawing the shaft of the (balloon) catheter by the other hand until the guide wire entry opening in the (balloon) catheter shank has reached the proximal end of the guide catheter. In the final portion of the distance, in which the guide wire extends within the shank (e.g. of a balloon catheter used in angioplasty), this process calls for a special technique to keep the wire from being accidentally withdrawn together with the (balloon) catheter. What this means is that the guide wire (because of its low resistance to buckling) has to be advanced step by step against the (balloon) catheter to the extent that the distal end of the latter (with the guide wire centrally extending therethrough) is withdrawn from the guide catheter. This procedure is relatively cumbersome and time consuming and requires the surgeon to pay utmost attention to what he/she is doing.

SUMMARY OF THE INVENTION

For the reasons outlined above, the object of the present invention is to provide structure which simplifies the difficult withdrawal of the catheter over a positioned guide wire.

A device of this kind is characterized by the features specified in the characterizing portion of patent claim 1.

One advantage of the inventive solution is that it substantially facilitates the surgeon's controlling the wire movement, i.e. the advancing movement of the wire and its simultaneous controlled rotation. It the same time, it is easier for the surgeon to distinguish the wire from the catheter shank so that both are easier to recognize and to handle, which is eminently important for rapid and safe treatment. The inventive device is equally suited for simplification and the improved withdrawal of coaxial wire-type catheters and so-called "monorail" catheters (wire preferably outside the cather shank) in a broad variety of catheter examinations of any organ system. It also facilitates the single-handed performance of such treatments, if it does not make them possible in the first place.

DETAILED DESCRIPTION OF THE INVENTION

Figure 1:
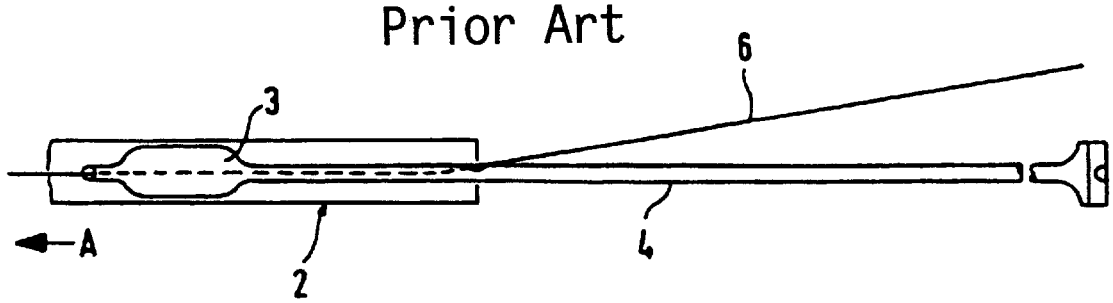
FIG. 1 is a side view of a conventional situation in which an inventive device is to be used on a patient.

The inventive device comprises a basic body adapted to be placed over guide wire 6. The body has a preferably central lumen 10 for receiving guide wire 6 and clamping means therefor, with body 9 having at its distal end a cannula-like extension 11, which may be telescoping if deemed necessary. The extent to which said cannula-like extension should be collapsible in telescope fashion corresponds in the case of a monorail catheter, for example, approximately to the length in which the guide wire extends centrally within the shank of the balloon catheter at the distal end thereof; that is, it corresponds to the distance between the entrance opening of the guide wire in the balloon catheter shank and its distal exit opening. The telescoping fashion of the cannula-like extension may be biased to extend by resilent pressure exerted by a means such as mechanical spring or gas. The compression of the cannula-like extension occurs through the succesive sliding of overlapping concentric tubular segments of the cannula-like extension 11. The length of the telescoping section may vary, however, depending on the specific diagnostic and therapeutic use to which the catheter is to be put. In its simplest form, the body may be force-locked to the guide wire by means of a knurled screw 13 or the like which exerts pressure on guide wire 6 extending centrally through basic body 9, thus clamping the wire against the opposite wall. In another embodiment, this clamping action may be provided by means operating in the manner of a conventional chuck of the kind used on power tools or lathes.

In a further embodiment, this clamping action may be actuated by a lever arm mounted on the basic body. When the lever arm is actuated, the lever arm releases the clamping means thereby clamping the guide wire. This actuation may also result in the release of the cannula-like extension for longitudinal movement relative to the basic body. When the lever arm is actuated again, the clamping means may release the clamping of the guide wire.

Figure 2:
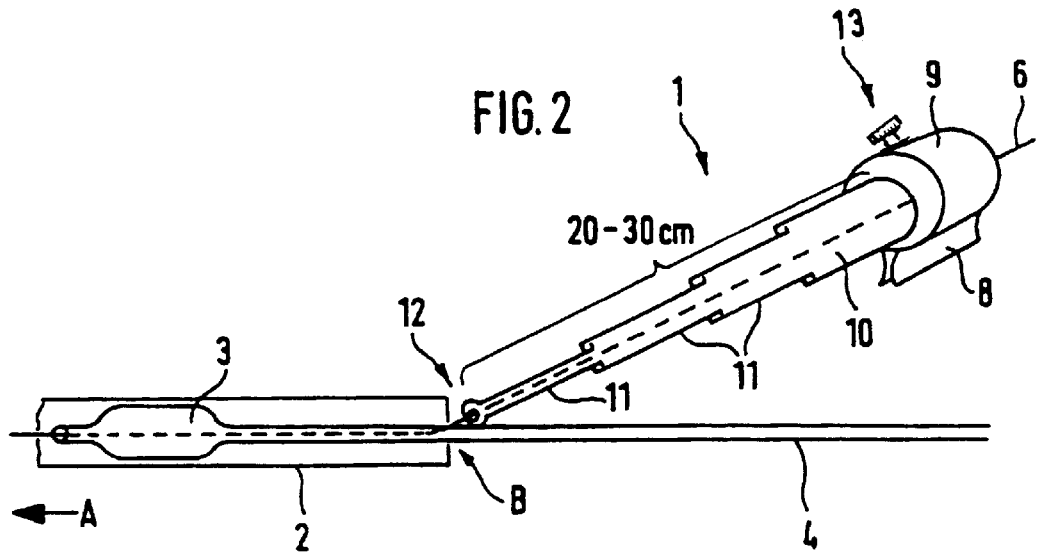
FIG. 2 is a perspective view of a preferred embodiment of the inventive device.

FIG. 1 of the drawing shows the conventional situation in which an inventive device is to be used on a patient, with both the guide catheter 2 and the guide wire 6 actually being much longer than shown in the drawing so as to be advanced to a patient's heart or other internal organ. As can be seen in the situation shown in FIG. 1, the balloon catheter cannot be withdrawn further from guide catheter 2 without at the same time withdrawing guide wire 6 because the latter extends inside the balloon catheter in the distal end portion thereof (shown in phantom). As the guide wire should maintain the position it has reached inside the heart or any other organ (see arrow A) even if a device such as balloon catheter 3 is withdrawn further, it is necessary for guide wire 6 to be advanced to the same extent as the balloon cather is being withdrawn. This process is difficult and error-prone, and it is the object of the present invention to improve on it. Such improvement is attained, for example, by the embodiment of the inventive device 1 shown in FIG. 2 in which guide wire 6 is placed before (balloon) catheter 3, 4 is withdrawn. As shown, the depicted embodiment of device 1 comprises an (elongated) basic body having a cannula-like extension 11 collapsible in telescope fashion, with means being provided to clamp guide wire 6 in position within body 9 (in a manner not shown in detail) so as to lock guide wire axially and circumferentially to body 9 as needed.

The expanded tip 12 at the end of the cannula-like extension 11 is expanded in an olive or mushroom shape so as to prevent its entry into the guide cathter 2. The expanded tip 12 may further have a crescent-shaped lateral recess for conformance with the shank of the baloon catheter 4.

Once the guide wire is locked in place, (balloon) catheter 3, 4 can be withdrawn from guide catheter 2 until the situation shown in FIG. 2 is reached once again, namely, that the point of balloon catheter is reached where guide wire 6 exits from balloon catheter 3, 4 (exit point B) and both exit jointly from guide catheter 2. In order to enable the (balloon) catheter to be further withdrawn from guide catheter 2 now, without guide wire 6 moving relative to the organ under treatment, the distal extension 11 or telescoping nose is collapsed to the extent that the extreme end of the (balloon) catheter is withdrawn further from guide catheter 2 so that ultimately no axial relative displacement of guide wire 6 takes place. Thereafter, the clamping lock of the guide wire in body 9 of the inventive device may be released (e.g. by actuating a lever arm) and device 1 be withdrawn from guide wire or moved along it, if desired. As a result, the novel device of the present invention improves, facilitates and accelerates the handling of the catheterizing process in its entirety, thus rendering it much safer.

In an alternative embodiment not shown in the drawing, the wire-receiving lumen of the of the device in its entirety—including body 9—has a lateral opening in the form of a longitudinally extending straight-line or undulating or spiralling slot. As a result, it is not necessary for wire 6 to be axially inserted end first into lumen 10; instead, it can be placed laterally through the aforesaid slot, so that the handling of the device is facilitated in certain applications.

What is claimed is:

1. A device for improving the handling of a catheter guide wire comprising:

a body having a proximal end and a distal end, wherein a wire receiving lumen extends longitudinally therethrough for receiving a guide wire, a clamping means for clamping a guide wire inside the longitudinally extending lumen, and a tubular extension projecting from the distal end of the body in the direction of the longitudinally extending lumen, wherein the tubular extension is adapted to be moved longitudinally relative to the body segment, and wherein the tubular extension is collapsible telescopically; and the wire receiving lumen extending longitudinally through the tubular extension to a distal opening defined by the tubular extension; and wherein the distal opening is sized to allow insertion of a guide wire into the wire receiving lumen and the wire receiving lumen is sized to allow a guide wire to extend through the device.

2. Device as in claim 1, wherein the clamping means is provided at the proximal end of the body segment.

3. A device for improving the handling of a catheter guide wire comprising:

a body having a proximal end and a distal end, wherein a wire receiving lumen extends longitudinally therethrough for receiving a guide wire, a clamping means for clamping the guide wire inside the longitudinally extending lumen, and a tubular extension projecting from the distal end of the body in the direction of the longitudinally extending lumen, wherein the tubular extension is adapted to be moved longitudinally relative to the body segment, and wherein the tubular extension is collapsible telescopically; and wherein the body has a sheet clamp, wherein the sheet clamp attaches to a sheet or drape.

* * * * *